(12) United States Patent
Iaizzo et al.

(10) Patent No.: US 6,714,806 B2
(45) Date of Patent: Mar. 30, 2004

(54) SYSTEM AND METHOD FOR DETERMINING TISSUE CONTACT OF AN IMPLANTABLE MEDICAL DEVICE WITHIN A BODY

(75) Inventors: Paul A. Iaizzo, White Bear Lake, MN (US); Timothy G. Laske, Shoreview, MN (US); Woohyek Choi, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/952,869

(22) Filed: Sep. 14, 2001

(65) Prior Publication Data
US 2002/0046756 A1 Apr. 25, 2002

Related U.S. Application Data
(60) Provisional application No. 60/234,058, filed on Sep. 20, 2000.

(51) Int. Cl.⁷ .................................................. A61B 5/04
(52) U.S. Cl. ....................... 600/374; 600/547; 600/375; 607/122; 607/126
(58) Field of Search .................................. 600/374, 375, 600/547, 548; 607/122, 126, 127, 131

(56) References Cited

U.S. PATENT DOCUMENTS

| | | |
|---|---|---|
| 2,702,354 A | 2/1955 | Chorpening |
| 3,894,532 A | 7/1975 | Morey |
| 4,351,345 A | 9/1982 | Carney |
| 4,444,195 A | 4/1984 | Gold |
| 4,591,668 A | 5/1986 | Iwata |
| 4,608,993 A | 9/1986 | Albert |
| 4,821,723 A | 4/1989 | Baker, Jr. et al. |
| 4,924,877 A | 5/1990 | Brooks |
| 4,936,310 A | 6/1990 | Engstrom et al. |
| 4,947,852 A | 8/1990 | Nassi et al. |
| 5,078,148 A | 1/1992 | Nassi et al. |
| 5,085,628 A | 2/1992 | Engebretson et al. |
| 5,131,388 A | 7/1992 | Pless et al. |
| 5,144,949 A | 9/1992 | Olson |
| 5,158,078 A | 10/1992 | Bennett et al. |
| 5,179,962 A | 1/1993 | Dutcher et al. |
| 5,199,428 A | 4/1993 | Obel et al. |
| 5,271,413 A | 12/1993 | Dalamagas et al. |
| 5,312,453 A | 5/1994 | Shelton et al. |
| 5,314,430 A | 5/1994 | Bardy |
| 5,324,321 A | 6/1994 | Pohndorf et al. |
| 5,330,507 A | 7/1994 | Schwartz |
| 5,331,966 A | 7/1994 | Bennett et al. |
| 5,333,614 A | 8/1994 | Feiring |

(List continued on next page.)

FOREIGN PATENT DOCUMENTS

| | | |
|---|---|---|
| EP | 0 841 073 B1 | 4/1993 |
| GB | 2 213 381 A | 8/1989 |
| WO | WO 93/09725 | 5/1993 |
| WO | WO 99 16350 A | 4/1999 |
| WO | WO 00/57805 | 10/2000 |

Primary Examiner—Rosalind K. Rollins
(74) Attorney, Agent, or Firm—Girma Wolde-Michael; Daniel G. Chapik; Michael C. Soldner

(57) ABSTRACT

An improved system for monitoring the status of an IMD such as a medical electrical lead during an implant procedure is provided. The system includes a signal generator for supplying a first signal such as a constant current or voltage to the IMD. A resulting voltage or current signal is generated, respectively, and may be sensed as an indication of the impedance of a portion of the body that is proximal to one or more electrodes carried by the lead. This impedance indication is converted to an audible signal having a frequency that is proportional to the amplitude of the impedance indication. The pitch of the audible signal therefore rises when measured impedance increases, and drops as the impedance decreases. These pitch changes allow a user to determine positional information associated with the IMD, including the degree of lead tissue contact and extent of fixation of a device to tissue.

20 Claims, 7 Drawing Sheets

U.S. PATENT DOCUMENTS

| | | |
|---|---|---|
| 5,335,668 A | 8/1994 | Nardella |
| 5,348,019 A | 9/1994 | Sluss, Jr. et al. |
| 5,353,800 A | 10/1994 | Pohndorf |
| 5,354,316 A | 10/1994 | Keimel |
| 5,387,233 A | 2/1995 | Alferness et al. |
| 5,396,902 A | 3/1995 | Brennen et al. |
| 5,427,144 A | 6/1995 | Teets et al. |
| 5,456,654 A | 10/1995 | Ball |
| 5,526,820 A | 6/1996 | Khoury |
| 5,545,186 A | 8/1996 | Olson et al. |
| 5,554,096 A | 9/1996 | Ball |
| 5,578,068 A | 11/1996 | Laske et al. |
| 5,643,255 A * | 7/1997 | Organ .................. 606/41 |
| 5,728,149 A | 3/1998 | Laske et al. |
| 5,741,214 A * | 4/1998 | Ouchi et al. ............ 607/122 |
| 5,788,647 A | 8/1998 | Eggers |
| 5,795,325 A | 8/1998 | Valley et al. |
| 5,873,835 A | 2/1999 | Hastings et al. |
| 5,888,187 A | 3/1999 | Jaeger et al. |
| 6,006,137 A | 12/1999 | Williams |
| 6,026,323 A | 2/2000 | Skladnev et al. |
| 6,064,905 A | 5/2000 | Webster, Jr. et al. |
| 6,174,278 B1 | 1/2001 | Jaeger et al. |
| 5,873,835 C1 | 8/2001 | Hastings et al. |

* cited by examiner

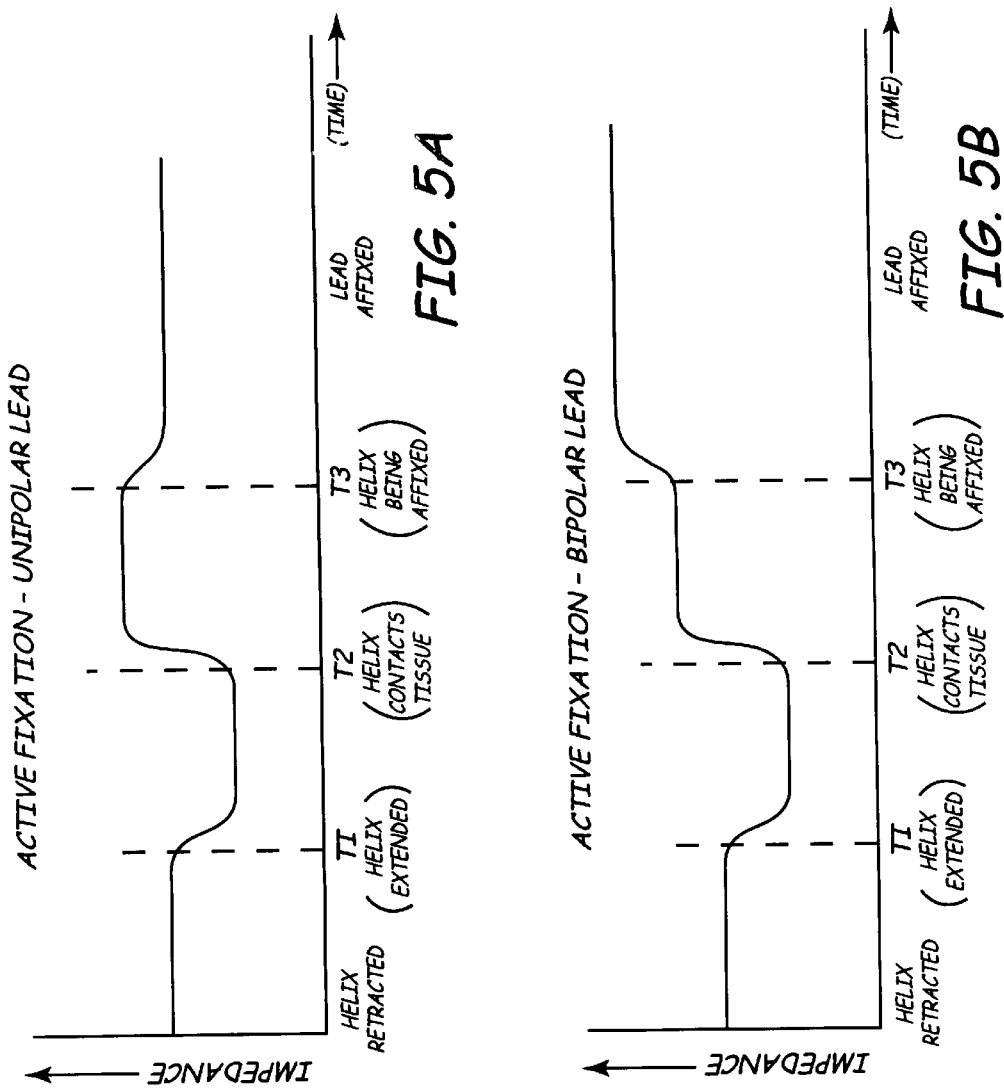

SYSTEM AND METHOD FOR DETERMINING TISSUE CONTACT OF AN IMPLANTABLE MEDICAL DEVICE WITHIN A BODY

RELATED APPLICATIONS

This application claims priority to provisionally-filed patent application serial No. 60/234,058 filed Sep. 20, 2000, which is incorporated herein by reference in its entirety.

FIELD

This invention relates generally to a system and method for placing implantable medical devices within a body; and more particular, relates to the use of audio signals for assessing status associated with an implantable medical device such as a lead during an implantation procedure.

BACKGROUND

Implantable medical devices such as electrical leads have long been employed in the fields of cardiac stimulation and monitoring. For example, leads are generally employed to deliver electrical stimulation for cardiac pacing and cardioversion/defibrillation applications. In these applications, endocardial leads are placed through a transvenous route to locate one or more sensing and/or stimulation electrodes in a desired location within a heart chamber or interconnecting vasculature. To provide effective therapy, electrodes carried at the lead distal end need to be accurately positioned at a predetermined location against the endocardium or within the myocardium. The lead distal tip is then generally affixed by a passive or active means to the tissue to maintain the desired location.

It is often difficult to determine whether a lead has been properly positioned and adequate tissue contact has been achieved. In some instances, catheters and leads are utilized that include materials that will allow for visualization with fluoroscopy. Additionally, fluoro-visible dyes may be injected into the cardiac chambers and venous anatomy so that the chambers of the heart and the related vasculature are visible using a fluoroscopic device. This procedure, sometimes referred to as a "venogram", allows the surgeon to locate a precise site and achieve proper electrode placement when performing an implant procedure.

Although the use of fluoro visible media is viable in some instances, this process has several disadvantages. First, some patients have adverse physical reactions when exposed to the fluoro visible dye used to obtain a venogram. Moreover, obtaining the venogram exposes the patient and clinicians to radiation. Additionally, a fluoroscope of the type needed for obtaining the fluoro-visible image may not be available. Finally, obtaining the venogram adds additional steps to the implant procedure, lengthening the time required to complete the procedure and increasing the risk of infection and complications to the patient.

An alternative method for determining the adequacy of tissue contact involves the use of impedance measurements. Since the impedance of fluids generally differs from that of tissue, impedance measurements may be used to determine whether an electrode has come in adequate contact with tissue.

Tissue impedance measurements are generally acquired by applying a known current or voltage signal to the tissue and measuring a resulting voltage or current, respectively. A system employing this method is disclosed in U.S. Pat. No. 5,447,529. A similar system is disclosed in U.S. Pat. No. 5,935,079 to Swanson et al., which describes a system to measure the electrical contact between the myocardium and multiple electrodes on a multiple electrode array. This Swanson system determines the amount of contact by transferring an electrical signal such as a current into the tissue so that tissue impedance may be measured.

Generally, when employing impedance measurements to assess tissue contact, the impedance signals are represented on some type of visual display for use by the clinician. However, because the impedance measurements and associated impedance changes are very small, the changes are difficult to detect visually. Moreover, because the physician is required to continually consult a monitor device for status, the physician must look away from the patient, diverting attention from the immediate task of manipulating the IMD into position. What is needed, therefore, is an improved system and method for assessing the status of an IMD such as a lead, and in particular, for assessing lead-to-tissue contact, during an implant procedure.

SUMMARY OF THE INVENTION

An improved system for monitoring the status of an IMD within a body is provided. In one embodiment, the IMD is a lead. The system includes a signal generator for supplying a first signal to the lead, which may be a constant current or voltage signal. A resulting voltage or current signal is generated, respectively, and may be sensed as an indication of the impedance of a portion of the body that is proximal to one or more electrodes carried by the lead. The impedance indication may then be converted to an audible signal. The audible signal has a frequency that is proportional to the amplitude of the impedance indication. The pitch of the audible signal therefore rises when measured impedance increases, and drops as the impedance decreases.

The inventive system provides an improved mechanism for monitoring the status of a lead or other IMD implanted within a body. Because impedance changes are converted to audible signals, the clinician need not utilize a visual display to detect the changes. This is advantageous because the clinician is allowed to focus all attention on manipulation of the IMD within the body, without having to divert attention to a display screen or other monitor. Additionally, the small changes in impedance are more readily detected using audible, rather than visual, means.

Many types of status indications may be detected using the current inventive system. For example, since the impedance between two electrodes at a lead distal tip changes as contact is made between the distal tip and cardiac tissue, tonal changes in the generated signal may be used to assess tissue contact. Moreover, impedance also changes as an active fixation device is embedded within tissue, causing tonal changes in the monitored audio signal useful for assessing the degree, and depth, of fixation. Similarly, the tonal changes may be used to detect over-torquing of a lead, which may cause wrapping of cardiac tissue around the lead tip such that impedance is increased. It may be further noted that tonal changes may be used to determine lead position within a body, since different types of tissue having different impedance values. Whether an extendable fixation mechanism is in a retracted or extended position may also be determined using tonal changes in the monitored audible signal. Finally, movement of a lead within a delivery catheter lumen can may be monitored using tonal changes in the monitored audio signal. For example, the tone changes as a tip and/or ring electrode carried by a lead are advanced beyond a catheter distal tip.

According to one embodiment of the invention, a system is provided for use in monitoring an implantable medical device (IMD) within a body. The system includes a first circuit to measure impedance of a portion of the body proximate a predetermined portion of the IMD. This first circuit may include a filter and amplifier to process the measured impedance indication. This signal may also be offset by a user-selectable amount during a calibration process, allowing the system to provide a predetermined audible signal when the IMD is in a predetermined state. This allows changes in the IMD status to be more readily detected.

According to another aspect of the invention, the system may include a processing circuit to process digitized samples of the measured impedance indication. Based on comparisons between the signal samples and predetermined criteria, the processing circuit develops an indication of the state of the IMD such as a lead and any associated fixation device. This indication may include information pertaining to tissue contact, the type of tissue being contacted, the extent of any tissue fixation, the position of an extendable/retractable fixation mechanism, and the position of an IMD relative to a delivery device such as a catheter. The data generated by the processing circuit may be provided to the user on an output device such as an LED display, a printer, or a display monitor. The data may be used to generate a virtual representation of the IMD within a patient's body.

Another embodiment of the invention involves a method for monitoring an IMD located within a body, including the steps of measuring a signal indicative of impedance within a portion of the body proximal the IMD, and generating an audible signal representative of the measured signal. The audible signal is then used to determine status associated with the IMD in the manner discussed above.

Other scopes and aspects of the invention will become apparent from the drawings and the accompanying description.

BRIEF DESCRIPTION OF THE DRAWINGS

FIG. 5A is a diagram illustrating impedance changes involving a unipolar lead having an active fixation mechanism.

FIG. 5B is a diagram illustrating impedance changes involving a bipolar lead having an active fixation mechanism.

DETAILED DESCRIPTION OF THE INVENTION

Figure 1:
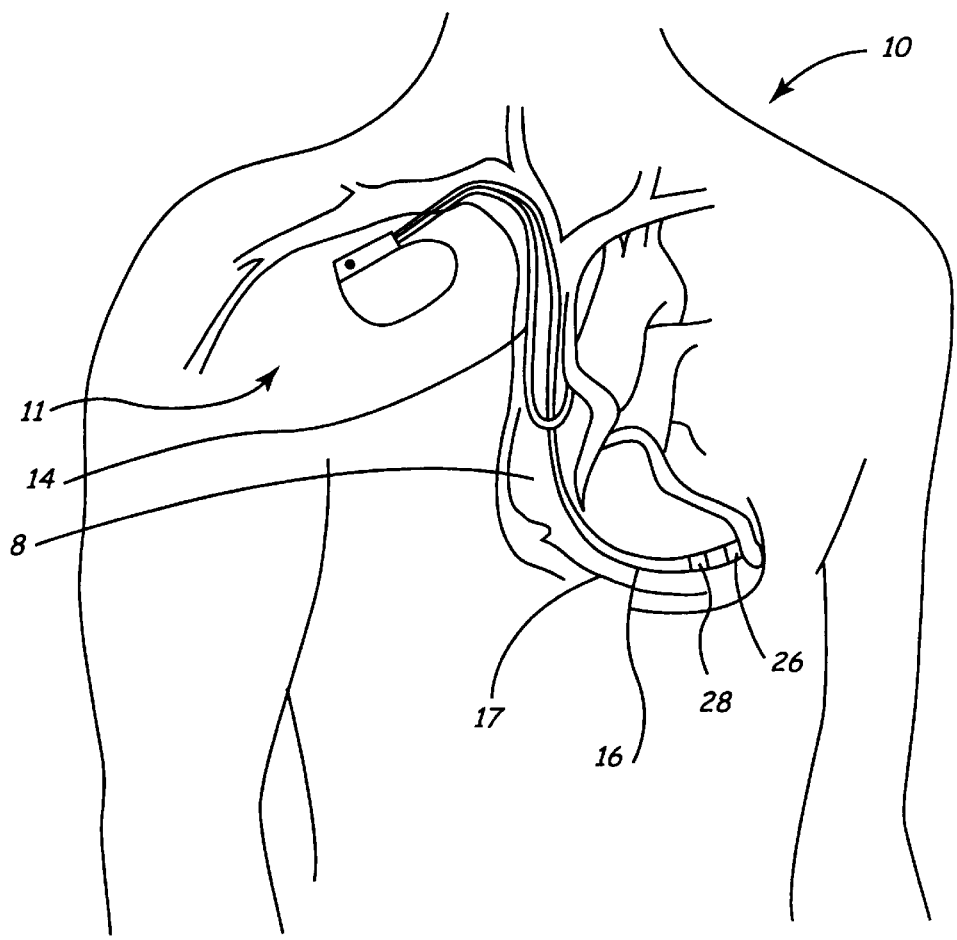
FIG. 1 is a diagram illustrating an implantable medical device (IMD) system implanted within a body of a patient.

FIG. 1 is a diagram illustrating an implantable medical device (IMD) system implanted within a body of a patient. The system includes a first lead 14 positioned in the right atrium and a second lead 16 positioned within the ventricle of heart 17. These leads are attached to IMD 11, shown implanted in the upper right chest of patient 10. These leads may include any of the passive or active fixation mechanisms known in the art, including tines or a fixation helix. Each of the leads may be bi-polar or unipolar, and may include one or more electrodes, such as a tip electrode 26 and ring electrode 28 of lead 16. The electrodes sense electrical signals attendant to the depolarization and repolarization of the heart, and may also transmit pacing pulses for causing depolarization of cardiac tissue in the vicinity of the electrode. These leads may each further include one or more high-voltage electrodes, and/or one or more additional sensors.

When positioning a lead within the heart as shown in FIG. 1, it is important to ensure adequate contact is made between the tip electrode and cardiac tissue. If adequate contact is not maintained, the heart tissue may not be appropriately affected by the delivered stimulation. The current invention provides an improved method for analyzing the adequacy of tissue contact without the need to utilize a fluoroscope.

Figure 2:
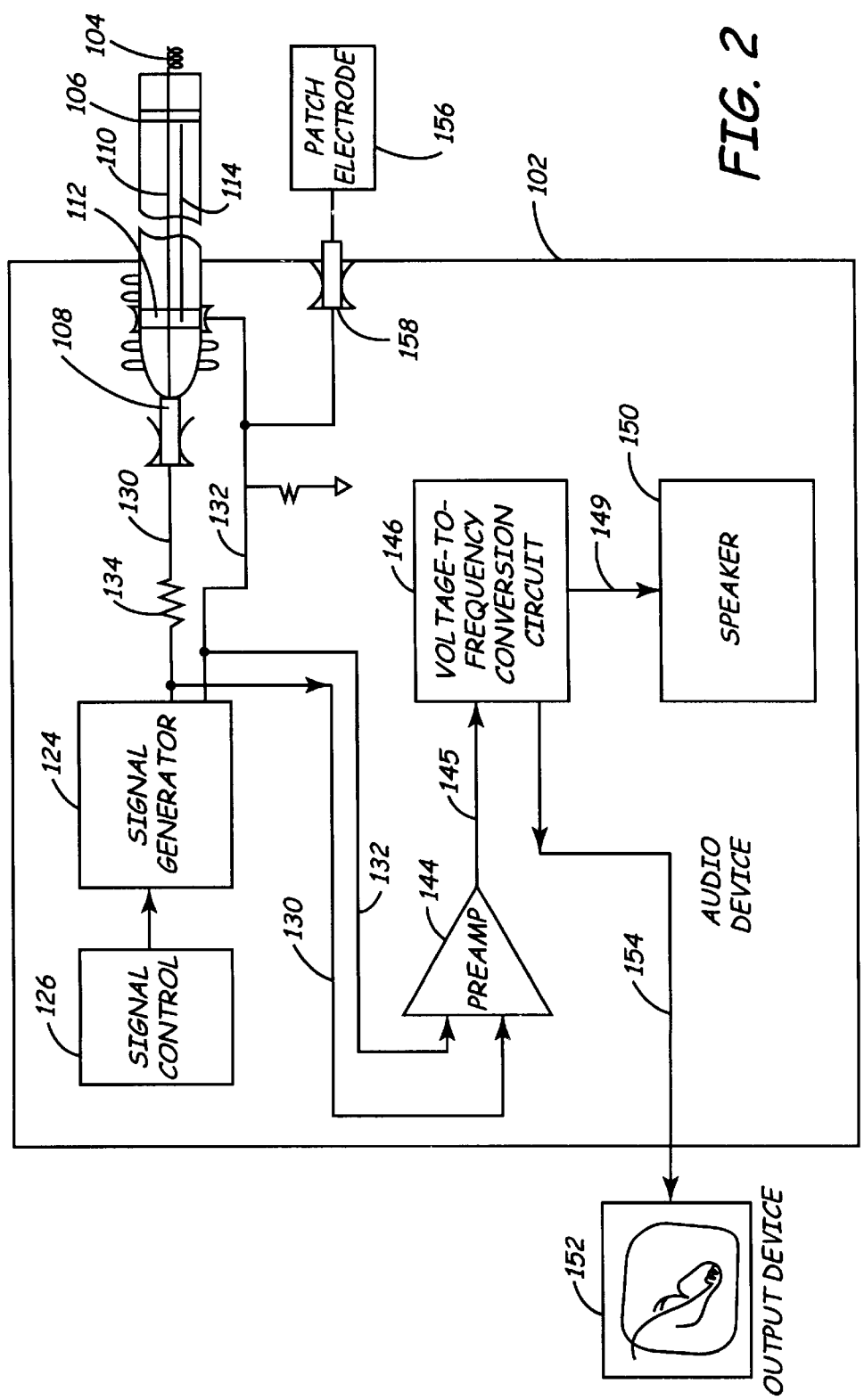
FIG. 2 is a block diagram of one embodiment of the current invention.

FIG. 2 is a block diagram of one embodiment of the current invention. An exemplary lead 100 is coupled to an audio device 102. Audio device is used to generate an audible signal representation of the impedance of the lead 100 at the lead distal tip as will be discussed below. Lead 100 is bipolar, including a fixation helix 104 and a ring electrode 106. The proximal end of lead 100 includes a pin connector 108 coupled electrically via conductor 110 to the fixation helix 104. Similarly, a ring connector 112 is coupled electrically via conductor 114 to ring electrode 106. Lead conductors 110 and 114 may each be of a cable or coiled configuration as is known in the prior art.

Pin connector 108 and ring connector 112 of lead 100 are coupled to respective connectors 120 and 122 of audio device. This allows the audio device to provide a current or voltage signal to the lead so that an impedance indication may be measured between the helix and the ring electrodes. More specifically, a constant current or voltage signal may be applied to conductors 130 and 110 by the signal generator 124. By then measuring the resulting voltage or current, respectively, across conductors 130 and 132, an indication of tissue impedance is obtained. This impedance indication may be used to detect the status of the lead, including the extent of tissue contact and fixation, in a manner to be discussed further below.

As noted above, to measure an indication of the tissue impedance, a constant voltage or current signal is applied to conductor 110. Because voltage detection is generally less complex than current detection, a constant current source is preferably selected as signal generator 124. In one embodiment, a Wien-Bridge oscillator is used for this purpose, although many other types of signal generators may be employed. To prevent shock that may result in fibrillation, the signal generator should include a current limiter. Additionally, both the amplitude and frequency of the current are maintained below predetermined upper limits to prevent inadvertent excitation or damage to the myocardial tissue.

The generated signal may be an AC or DC signal. However, because cardiac signals include frequency components between approximately DC and 300 Hz, a sinusoidal signal in the range of 1 KHz is preferred. Signal characteristics may be made user-selectable by providing signal control circuit 126, which may interface to user controls for selecting amplitude, frequency, and/or waveform type, if desired.

The current is supplied through resister 134, which is selected so that the myocardial resistance is below 10% of the resistance of resister 134. In one embodiment, a current of 100μ Amps is supplied through resister 134 having a value of 100 KΩ. In another embodiment, a current of 500μ Amps is supplied through resister 134, which is selected to have a value of 20 KΩ. Finally, the various components of audio device 102 are selected so that the input impedance is very high as compared to the myocardial impedance. This results in minimal signal distortion. In one embodiment, the input impedance of audio device 102 is at least 10 MΩ.

During operation, the current signal is provided on conductor 130, while conductor 132 is maintained at ground. When the lead is implanted within a body, the current flows via conductors 10 to the tip electrode, which in this instance is fixation helix 104. Current flow continues into the surrounding tissue and bodily fluid to ring electrode 106, which is grounded via the connection to the audio device. This flow results in a voltage differential that is measured in a manner to be discussed below.

As discussed above, the flow of current on conductors 130 and 132 results in a voltage differential on the inputs of pre-amplifier circuit 144. This pre-amplifier is configured to amplify the signal between five and ten times, which is a gain selected to optimize signal to noise ratios. Many types of instrumentation amplifiers may be adapted for use as a pre-amplifier circuit, such as the INA 114 instrumentation amplifier commercially available from Texas Instruments, Inc.

The signal generated by the pre-amplifier circuit 144 is provided on line 145 to a voltage-to-frequency conversion circuit 146 that filters and further amplifies the voltage signal. This voltage signal is converted to a signal having a frequency proportional to the voltage, and which is in a frequency range that is audible to the human ear. This frequency signal is provided on line 149 to speaker 150. Many types of speakers may be selected for use within the system. In one embodiment, the speaker is a piezoelectric speaker having a forty-volt peak-to-peak output range.

The current system aids a physician during an implant procedure by providing a readily-discernable audio indication of lead distal tip status, as well as lead-to-tissue contact. For example, assume a bipolar lead having an active fixation mechanism as shown in FIG. 2 is being implanted within a patient. With the helix in a retracted position and the lead maintained in a stationary position suspended in blood within a cardiac chamber, the measured impedance will remain relatively constant. Therefore, a substantially constant tone is provided by speaker 150 to the user. When the helix is extended, the impedance will decrease, resulting in a corresponding decreased frequency of the signal provided on line 149 to speaker 150. As a result, the pitch of the tone generated by speaker will noticeably drop, alerting the clinician of helix extension. Next, as the lead contacts tissue, impedance increases, causing the audible tone to rise. Finally, as the helix is affixed to the tissue, impedance increases even further, resulting in another rise in the pitch of the signal produced by speaker 150.

The tonal changes discussed above provide a simplified indicator of the status of a fixation device during an implant procedure. Prior art systems measuring impedance changes are difficult to use. Often, the impedance changes are small, and are therefore difficult to detect when using a monitor to display a signal indicative of the impedance changes. Moreover, the clinician must frequently divert attention from the procedure at hand to consult the display, making the procedure more difficult. Using the current system, even small changes in impedance can be readily detected by resulting tonal changes in the audible signal. These changes may be detected without the need to consult a monitor. The physician is therefore allowed to focus attention on lead manipulation, making the implant procedure less difficult and more efficient.

Although FIG. 2 illustrates use of a bipolar lead, the system may be employed with a unipolar lead. In that instance, the ring electrode 114 is not available as the return current path. Instead, this path may be provided by a patch electrode 140, which may be coupled to a patient's chest and connected to a supplemental connector 142 of the audio device. In another embodiment wherein the inventive system is utilized with an implantable pulse generator in a manner to be discussed below, the pulse generator can may provide the return current path.

FIG. 2 further illustrates an output device 152, which may include a display monitor, a printer, and/or another type of display such as an LED display. This output device, which optionally may be an integral part of audio device 102, may receive a signal on line 154 that is indicative of the impedance change. This signal is used to provide an additional indication of lead status. For example, in the event the output device is a display monitor, the monitor may display the amplified voltage signal at a given period in time, or may alternatively, provide a refreshed representation of the changes in the signal over a predetermined period in time. In one embodiment, the signal level on line 154 may be generated by a processing circuit to be discussed below. The processing circuit monitors the changes in the measured impedance to generate a virtual image of the lead on a display monitor. Alternatively, or additionally, output device 152 may include an LED display to provide an indication of the real-time signal level, or a graphical output display indicating changes in the monitored signal. A printer may also be provided to generate a hard-copy output of the lead status.

Finally, it may be noted that although FIG. 2 illustrates use of a bipolar lead, the system may be employed with a unipolar lead. In that instance, the ring electrode 114 is not available as the return current path. Instead, this path may be provided by a patch electrode 156, which may be coupled to a patient's chest and connected to a supplemental connector 158 of the audio device.

Figure 3:
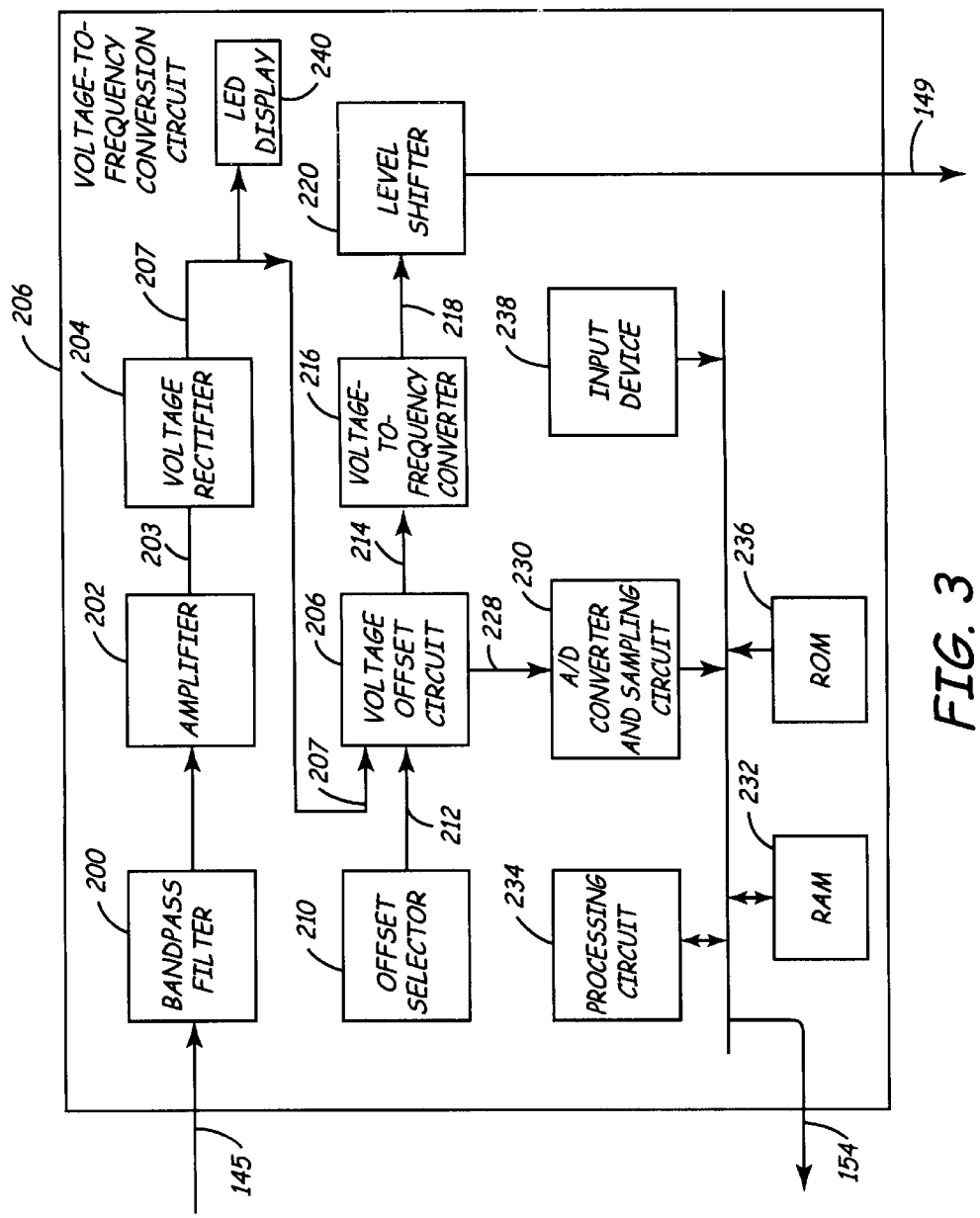
FIG. 3 is an exemplary embodiment of the voltage-to-frequency conversion circuit of FIG. 2.

FIG. 3 is an exemplary embodiment of voltage-to-frequency conversion circuit 146 of FIG. 2. An amplified voltage signal is received on line 145 from pre-amplifier 144 (FIG. 2). This signal is provided to bandpass filter 200. Bandpass filter 200 is adapted to pass signals having a frequency around 1 KHz. A passive RLC filter having a 100 Hz bandwidth may be selected to provide this functionality.

The signal provided by bandpass filter 200 is provided to a main amplifier circuit 202, which amplifies the signal by an amount that is dictated by system limitations, including the maximum supply voltage level. In one embodiment, the maximum supply voltage level is ten volts, and signal amplification is thereby selected to provide a signal amplitude between plus and minus ten volts. Many amplification circuits are available for use in this manner. For example, the OPA27 operational amplifier circuit commercially available from Texas Instruments, Inc., may be selected for this purpose.

The amplified signal is provided on line 203 to a voltage rectifier 204. This circuit, which may be a full-wave or half-wave rectifier, converts the AC voltage signal on line 203 to a substantially DC voltage level on output line 207. One simple embodiment of a half-wave rectifier comprising a diode, resistor, and catheter as is known in the art. The rectifier utilized within the current invention is selected to have a fast response time and to provide an output signal having a very low ripple. This results in generation of audible tones that maintain a consistent pitch during periods when the impedance levels measured across the lead tip are remaining substantially constant.

Voltage rectifier 204 provides a signal to a voltage offset circuit 206 on line 207. Voltage offset circuit may be used to "zero" the device when the lead is in at a predetermined state within the body. For example, when the lead is maintained at a position that is suspended in bodily fluid not contacting tissue, and with the helix in a retracted state, the user may adjust the offset selector 210 to provide a predetermined voltage level on line 212 to voltage offset circuit 206. Voltage offset circuit 206 then generates a voltage signal on line 214 having an amplitude that is substantially the difference between the voltage signals on lines 207 and 212. In this manner, the user can adjust offset selector 210 so that a particular tonal value is associated with the predetermined known state, which in this example is a suspended distal tip having a retracted helix. Alternatively, the user can adjust the offset selector so that a voltage of zero is provided on line 214 when the lead is in a predetermined state so that no audible tone is generated until impedance increases. Voltage offset circuit 206 may be implemented using an INA 114 instrumentation amplifier available from Texas Instruments, Inc.

The signal on line 214 is provided to a voltage-to-frequency converter 216, which, in turn, generates a signal on line 218 that has a frequency proportional to the voltage on line 214. Depending on the type of circuit utilized for the voltage-to-frequency converter, a signal may be provided on line 218 that is entirely one polarity. For example, the signal may be entirely positive-going. To drive speaker 150 (FIG. 2), the signal on line 218 must be level-shifted to include positive and negative components. This is accomplished using level shifter 220. Level shifter 220 of a first embodiment may comprise a capacitor. Alternatively, level shifter 220 of a second embodiment may include a comparator circuit that receives the signal on line 218 as one input. A constant voltage amplitude that is approximately halfway between the minimum and maximum voltages of the signal on line 218 is selected as the other input. This causes the comparator to generate a signal on line 149 that has a frequency substantially equal to the signal on line 218, but which eliminates the DC offset voltage. Moreover, this signal will toggle between the voltage ranges allowed by the power supply. For example, if a power supply supplying between plus and minus twelve volts is supplied to comparator, the resulting waveform toggles substantially between these two voltage ranges. Therefore, as compared to the first embodiment, this second embodiment has the advantage of providing maximum drive capability for speaker 150.

FIG. 3 also includes an optional processing circuit. This circuit may comprise an analog-to-digital (A/D) converter 230. A/D converter 230 receives a voltage waveform on line 228, and in turn, generates digital samples of the waveform that may be stored in random-access memory (RAM) 232. These samples can be analyzed by processing circuit 234, which executes under the control of microcode stored in RAM and/or read-only memory (ROM) 236. The processing circuit may analyze the changes in the digitized stored signal over time. Additionally or alternatively, the processing circuit may analyze the samples as compared to a sample pattern stored in memory. The sample pattern may represent expected impedance changes for a particular type of lead as an implantation procedure progresses.

Based on the analysis performed by the processing circuit 234, signals can be provided on line 154 to generate a display. The display may include a virtual representation of the current state of the lead within the body based on the status determined by the processing circuit. This display can be generated on output device 152, which may include a display monitor as discussed above. Alternatively, any other type of display indicative of the status of the implantation procedure may be provided on output device 152 under the control of the processing circuit 234. According to one embodiment, the voltage signal provided on line 207 by voltage rectifier 204 may also be displayed, as on LED display 240. Other voltage levels may be displayed, if desired, such as the voltage provided on line 214.

The processing circuit may receive input from one or more input devices 238. These input devices are needed to indicate to the processing circuit which type of lead, lead delivery system, and/or fixation mechanism are being employed during a given implantation procedure. The input device may include a keyboard, mouse, touch screen, one or more knobs, dials, pushbuttons, and/or another other type of input device known in the art. The use of the user-provided data is discussed further below.

The impedance variations associated with an implantation procedure vary depending on the type of lead and lead delivery system being utilized, as well as the type of fixation mechanism used with the lead. The following discussion describes the impedance variations associated with several commonly-used medical electrical lead configurations.

Figure 4A:
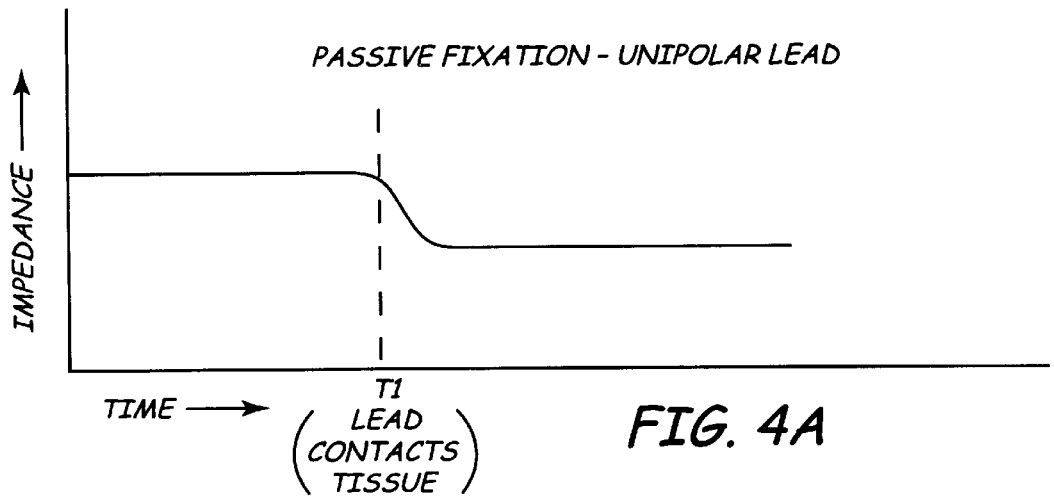
FIG. 4A is a diagram illustrating impedance changes involving a unipolar lead having a passive fixation mechanism.

FIG. 4A is a diagram illustrating impedance changes during an implantation procedure employing a unipolar lead having a passive fixation mechanism such as tines located at the lead distal tip. Prior to time T1, the distal tip of the lead including the fixation mechanism is suspended in a cardiac chamber. At time T1, contact is made with myocardial tissue, resulting in a drop in the measured impedance level. This drop in impedance occurs because the flow of current back to the measurement system such as audio device 102 is actually aided by the tissue contact. According to the present invention, the drop in impedance will be associated with a corresponding drop in the pitch of the audible sound produced by speaker 152, alerting the clinician to the tissue contact. Additionally, the unstable lead distal tip position associated with the tissue contact will result in varying tonal values in the audible signal, whereas when no tissue contact is occurring, the generated tones will remain relatively constant.

It may be noted that the impedance change associated with tissue contact varies with the type of tissue being contacted. This is true whether passive or active fixation mechanisms are utilized. The measured impedance of the tissue therefore provides an indication of lead location within the vascular system. Impedance measurements also provide an indication of the health of the tissue, since tissue damage due to an infarct and/or the on-set of certain cardiac conditions result in impedance changes within the tissue.

Figure 4B:
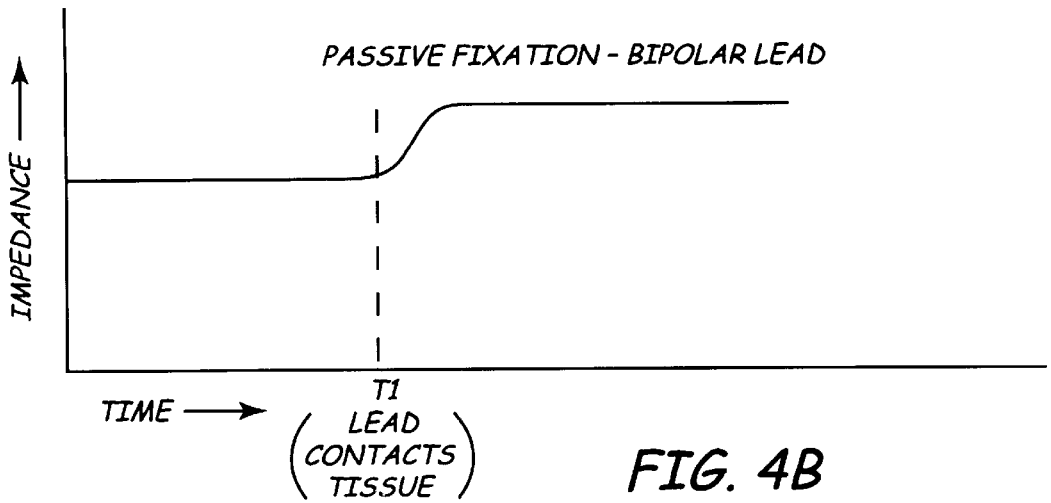
FIG. 4B is a diagram illustrating impedance changes involving a bipolar lead having a passive fixation mechanism.

FIG. 4B is a diagram illustrating impedance changes during an implantation procedure employing a bipolar lead having a passive fixation mechanism. During time T1, the distal lead tip is suspended in blood. At time T1, contact is made with myocardial tissue, resulting in an increase in impedance. This occurs because current flow between tip and ring electrodes is impeded by the intervening tissue contact. This increase in impedance is accompanied by a corresponding rise in the pitch of the audible signal.

FIG. 5A is a diagram illustrating impedance changes during an implantation procedure employing a unipolar lead having an active fixation mechanism such as a fixation helix located at the lead distal tip. Prior to time T1, the distal tip of the lead is suspended in a cardiac chamber with the helix retracted. At time T1, the helix is extended, causing the impedance to drop. At time T2, the lead is positioned so that the helix contacts the myocardial tissue, causing the impedance to increase. At time T3, the helix is advanced into the tissue, causing the impedance to again drop. The tonal changes may be used to determine the extent of the helix fixation.

As is known in the art, one mechanism for determining whether a fixation mechanism has been attached to the tissue is by monitoring what is known as "the current of injury". This phenomenon, which is the body's natural physical response to injury, involves a voltage potential difference that is set up within body tissue that has suffered damage. Some physicians monitor this phenomenon to determine whether an active fixation device has penetrated the myocardium. However, this mechanism does not allow a user to assess the degree of tissue penetration. The current invention provides an improved mechanism for determining the depth that an active fixation device is embedded into the tissue.

FIG. 5B is a diagram illustrating impedance changes during an implantation procedure employing a bipolar lead having an active fixation mechanism. Prior to time T1, the distal tip of the lead is suspended in a cardiac chamber with the helix retracted. At time T1, the helix is extended, causing the impedance to drop. At time T2, the lead distal tip is positioned so that the helix contacts the myocardial tissue, causing the impedance to increase. At time T3, the helix is advanced into the tissue, causing the impedance to again increase.

The increases and decreases in impedance illustrated in FIG. 5 are each accompanied by an increase or decrease in the pitch of the tone generated by speaker 150. This alerts the educated user as to the status of lead distal tip, including the extent of tissue contact associated with the fixation mechanism.

Figure 6:
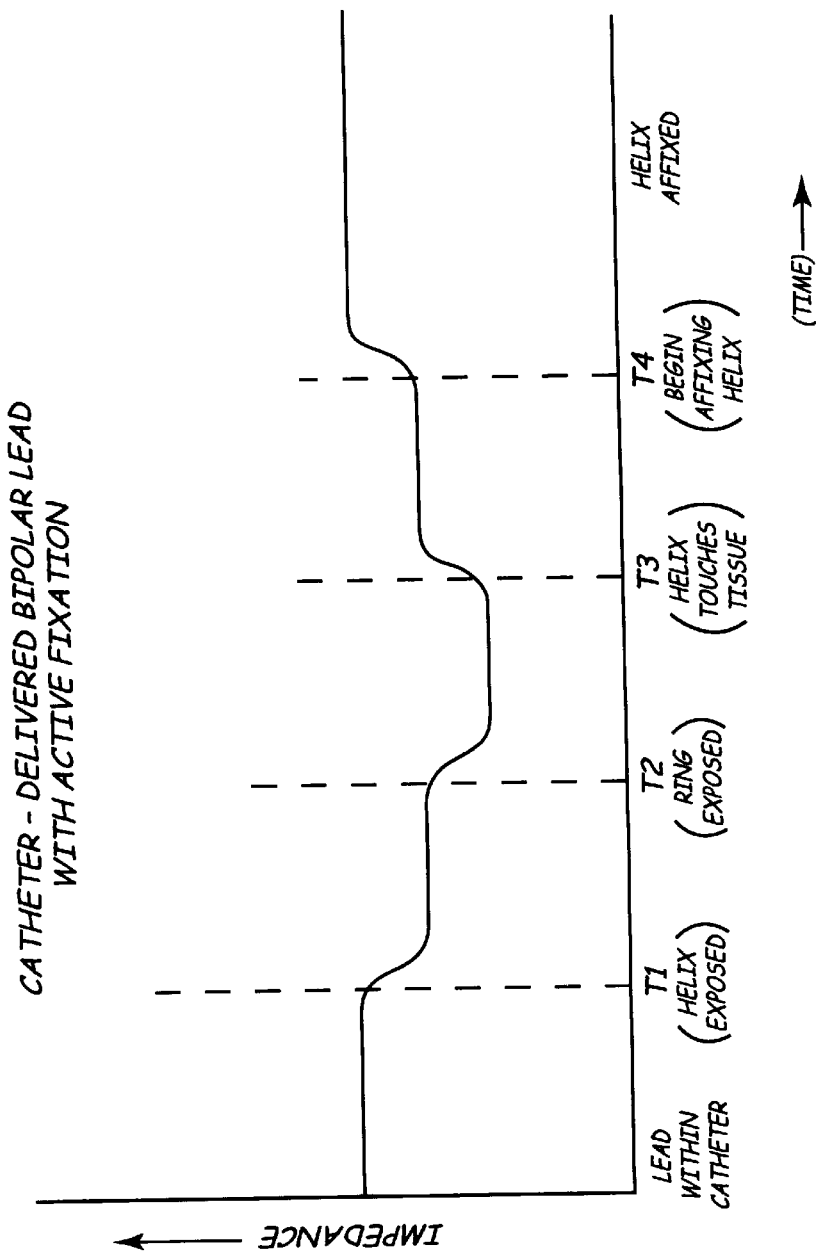
FIG. 6 is a diagram illustrating impedance changes involving a catheter-delivered, bipolar lead having an active fixation mechanism.

FIG. 6 is a diagram illustrating impedance changes involving a catheter-delivered, bipolar lead having an active fixation mechanism. Prior to time T1, the lead is within a lumen of the catheter with the helix extended, and the catheter is suspended within a cardiac chamber. At time T1, the lead is advanced within the catheter lumen such that the helix extends beyond the catheter distal tip, resulting in a decrease in the measured impedance value. At time T2, the ring electrode of the lead is extended beyond the catheter distal tip, resulting in an additional decrease in the impedance. At time T3, the helix touches tissue, causing an increase in impedance. At time T4, the helix is advanced into the tissue, resulting in an additional increase in the measured impedance. In a manner similar to that discussed above, each increase and decrease in impedance is associated with a corresponding pitch increase or decrease, respectively, of the audible signal.

As noted above, the type of delivery system, lead, and fixation mechanism affects the type of impedance profile that can be expected when the lead is delivered. Each type of lead, delivery system, and fixation mechanism is associated with a unique impedance profile in a manner similar to that discussed above. Thus, when using microprocessor-based analysis as discussed in reference to FIG. 3 above, the type of lead and delivery system must be selected for use by the processing system during the analysis, as may be accomplished using input devices 238 (FIG. 3).

Figure 7:
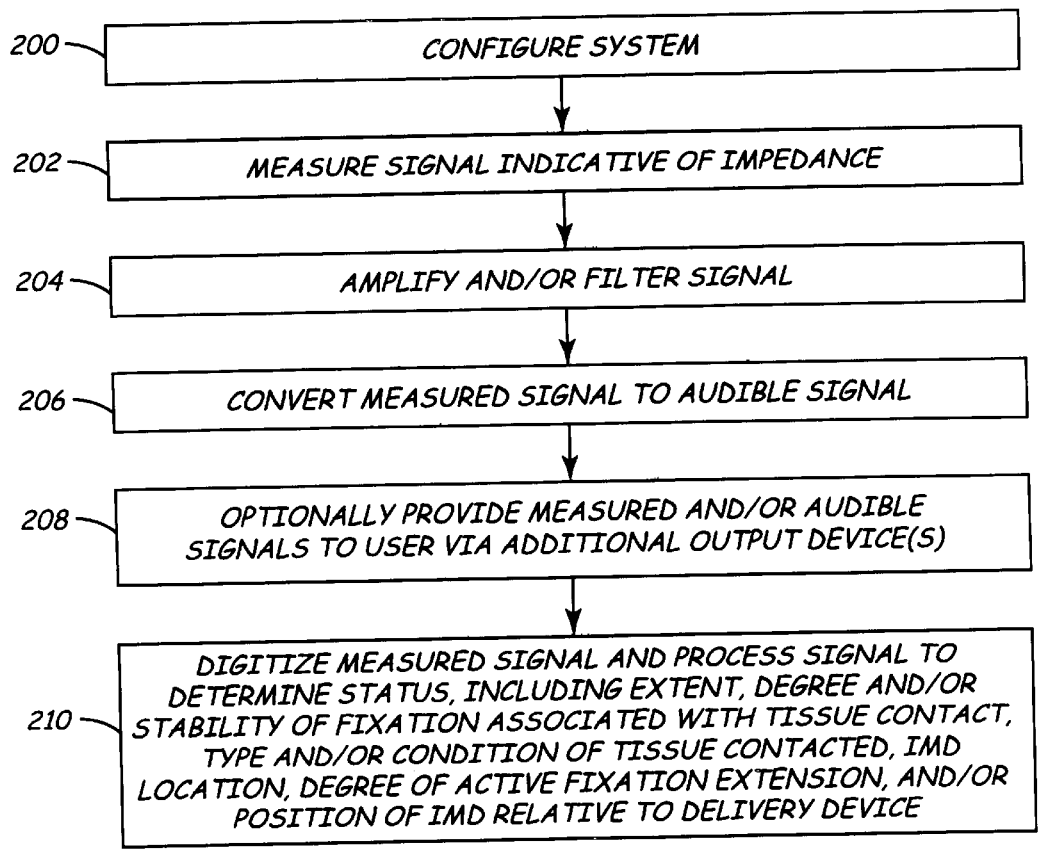
FIG. 7 is a flow diagram illustrating one embodiment of the current invention.

FIG. 7 is a flowchart illustrating one embodiment of the current invention. The system may be configured for a particular lead, fixation mechanism, and delivery system utilizing a user interface such as input device 238 (200). A first signal may be provided to an IMD, and a second signal indicative of impedance in a portion of the body proximal the IMD may be measured (202). The signal may be filtered and/or amplified (204), then converted to a signal having a frequency proportional to the amplitude of the measured signal and which is in the audible range (206). This signal is provided to the user using a speaker or other similar device. This may be accomplished using a voltage-to-frequency signal converter, as discussed above. Additionally, a representation of the measured signal and/or the audible signal may be provided to the user via one or more additional output devices such as a printer, a graphical display, a display monitor, or any other type of output device known in the art (208).

The measured signal may be digitized and processed by a processing circuit (210). This analysis may involve comparing the measured signal to stored acoustic patterns in memory, using a rules-based analysis, or using some other type of analysis mechanism. Based on this analysis, additional status information may be developed by the processing circuit, and provided to an output device. This additional status information, as well as the audible signal, may provide information related to extent, stability, and/or degree of fixation associated with tissue contact, the type and condition of the tissue that is being contacted by an IMD, the IMD location, the degree of extension associated with a retractable active fixation mechanism, and the position of the IMD in relation to a delivery system.

The above-described device may be embodied as a stand-alone device, or may be incorporated into a programmer such as the Model 9790 programmer commercially-available from the Medtronic corporation. Additionally, the system may be utilized with a catheter to measure catheter tip impedance, or any other type of implantable device that delivers electrical stimulation to tissue, or that has a conductive member or electrode at a distal end. Although the above exemplary description relates to use of the invention within the cardiovascular system, it may be equally useful in navigating any other portion of the body. Many alternative embodiments of the inventive system are possible and will be apparent to those skilled in the art. For example, many of the various circuits illustrated in FIGS. 2 and 3 are largely optional. Offset selector 210 and voltage offset circuit 206 are not necessary, and may be eliminated. Similarly, the processing circuit 234 and accompanying circuitry is optional. Therefore, it will be understood that the scope of the invention is to be determined by the structures and methods set forth in the following claims.

What is claimed is:

1. A system for use in monitoring an implantable medical device (IMD) within a body, comprising:
   a first circuit to couple to the IMD to measure an indication of impedance of a portion of the body proximate a predetermined portion of the IMD;
   an audio circuit coupled to the first circuit to generate an audible signal representative of the measured impedance;

a display monitor coupled to the first circuit to provide an indication of the measured impedance; and a processing circuit coupled to receive a signal indicative of the impedance of the portion of the body, and to provide status indicative of the IMD based on the received signal to the display monitor to create a virtual image of the IMD in the body, wherein the IMD is a lead that includes a fixation mechanism, and wherein the processing circuit includes means for generating status indicative of the extent of contact between a predetermined portion of the lead and the body and further includes means for generating status descriptive of the fixation mechanism.

2. The system of claim 1, wherein the lead is delivered to the body using a delivery system, and wherein the processing circuit includes means for generating status descriptive of a position of the lead in relation to the delivery system.

3. The system of claim 1, wherein the first circuit includes a voltage-to-frequency converter.

4. The system of claim 3, and further including an offset circuit coupled to provide an indication of the measured impedance to the voltage-to-frequency converter, the indication of the measured impedance being offset by a predetermined selectable amount.

5. The system of claim 1, wherein the first circuit further comprises a signal generator to provide a first signal to the IMD, and whereby a second signal indicative of the impedance is generated as an input to the first circuit.

6. The system of claim 5, wherein the signal generator is selected from the group consisting of a current source and a voltage source.

7. A method for monitoring a lead, having a fixation device, located within a body, comprising the steps of:

a.) measuring a signal indicative of impedance within a portion of the body proximal the lead;

b.) generating an audible signal representative of the signal measured in step a.); and c.) utilizing the audible signal to determine status of the lead and to determine the extent of contact between the tissue and the fixation device.

8. The method of claim 7, and further including utilizing the audible signal to determine the extent of fixation between the tissue and the fixation device.

9. The method of claim 8, wherein the lead is delivered with a delivery system, and further including utilizing the audible signal to determine orientation of the lead with respect to the delivery system.

10. The method of claim 7, wherein step a.) includes providing a predetermined first signal to the IMD to generate the signal indicative of impedance.

11. The method of claim 10, wherein step a.) includes filtering the signal indicative of impedance.

12. The method of claim 11, wherein step a.) includes amplifying the signal indicative of impedance.

13. The method of claim 12, wherein step a.) includes offsetting the signal indicative of impedance by a selectable offset value.

14. The method of claim 7, wherein step b.) includes generating a signal having a frequency proportional to the amplitude of the signal indicative of impedance.

15. The method of claim 7, and further including providing a processing circuit to determine the status of the IMD.

16. The method of claim 7, and further including providing the status of the IMD to an output device.

17. The method of claim 16, wherein the output device is a display monitor, and further including providing an image of the IMD located within the body on the display monitor.

18. The method of claim 7, wherein determining status of the IMD includes utilizing input signals that are provided by a user to determine the type of the IMD.

19. The method of claim 7, and further including utilizing the audible signal to determine the type of, or condition of, tissue in the portion of the body proximal the IMD.

20. The method of claim 7, wherein the IMD has a distal tip, and further including utilizing the audible signal to determine stability of a position of the distal tip with respect to the portion of the body proximal the IMD.

* * * * *

UNITED STATES PATENT AND TRADEMARK OFFICE
CERTIFICATE OF CORRECTION

PATENT NO. : 6,714,806 B2
DATED : March 30, 2004
INVENTOR(S) : Paul A. Iaizzo et al.

It is certified that error appears in the above-identified patent and that said Letters Patent is hereby corrected as shown below:

Title page,
Item [73], Assignee, after "Minneapolis, MN (USA)" please insert -- ; University of Minnesota, Minneapolis, MN (USA) --.

Signed and Sealed this

Twenty-first Day of December, 2004

JON W. DUDAS
*Director of the United States Patent and Trademark Office*